United States Patent [19]
Quackenbush

[11] Patent Number: 4,900,314
[45] Date of Patent: Feb. 13, 1990

[54] COLLAPSE-RESISTANT TUBING FOR MEDICAL USE

[75] Inventor: John Quackenbush, Hoover, Ala.

[73] Assignee: FBK International Corporation, Birmingham, Ala.

[21] Appl. No.: 151,030

[22] Filed: Feb. 1, 1988

[51] Int. Cl.$^4$ .............................................. A61M 25/00
[52] U.S. Cl. ...................................... 604/282; 604/45
[58] Field of Search ................................... 604/43–45, 604/280–283

[56] References Cited

U.S. PATENT DOCUMENTS

| | | | |
|---|---|---|---|
| 1,596,754 | 8/1926 | Moschelle | 604/282 |
| 3,034,510 | 5/1962 | Kittel | 604/101 |
| 3,963,856 | 6/1976 | Carlson et al. | 604/280 X |
| 4,498,473 | 2/1985 | Gereg | 128/207.15 |

Primary Examiner—Dalton L. Truluck

[57] ABSTRACT

A collapse-resistant catheter adapted for medical usage includes a central tube having a smooth outer wall rather than a corrugated outer wall characteristic of prior art collapse-resistant catheters. The tube includes an integral, spiral-shaped outer tube which provides the collapse-resistant characteristic. The spiral tube also provides an additional lumen. The center tube is adapted to provide for a multilumen structure not possible with corrugated prior art structures. The resulting structure, single or multilumen, can be made sufficiently small for insertion into the human body.

6 Claims, 3 Drawing Sheets

41

51

61

COLLAPSE-RESISTANT TUBING FOR MEDICAL USE

FIELD OF THE INVENTION

This invention relates to tubing for medical usage and more particularly to small diameter tubing which are collapse resistant.

BACKGROUND OF THE INVENTION

Collapse resistant tubing particularly for air delivery in medical procedures typically comprises a single lumen tube the wall of which has a crenellated cross section imparting to it a corrugated geometry. Although such tubes are in widespread use, they are difficult to make small, they do crimp, they do cause turbulence in the flow of material through them, and they cannot be made in an integral multilumen configuration.

BRIEF DESCRIPTION OF EMBODIMENTS OF THIS INVENTION

The invention is based on the realization that all the advantages of a corrugated tube can be retained while all the disadvantages can be eliminated by an alternative tube configuration. The alternative tube configuration comprises, in one embodiment, a single center lumen with, for example, a smooth circular wall and a second tube attached to the outer surface of that wall and following a spiral path about that wall. The second tube not only provides rigidity, but resists crimping, avoids turbulence and provides a secondary path or lumen which may be used, for example, to withdraw fluids.

The second tube is produced by coextrusion techniques where a rotating die delivers a second extrudate downstream of a previously extruded smooth outer wall of the center tube. Further, the center tube itself can be made of a multilumen configuration, a structure not possible with prior are collapse-resistant tubing.

DETAILED DESCRIPTION

Figure 1:
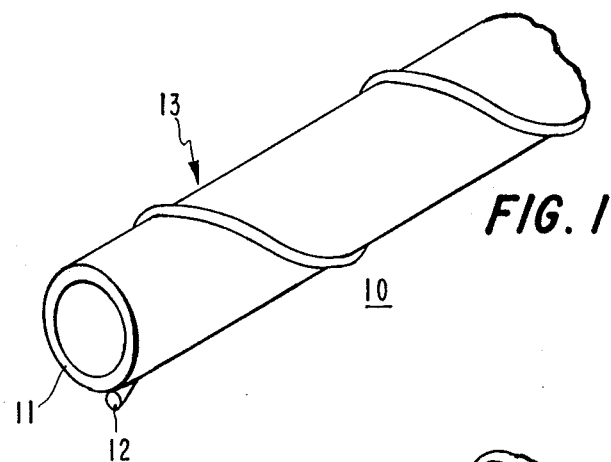
FIGS. 1 and 2 are schematic representations of collapse resistant catheters in accordance with the principles of this invention.

FIG. 1 shows a collapse-resistant catheter 10 in accordance with the principles of this invention. Cathether 10 includes a single lumen center tube 11 and a spiral-shaped, outer tube 12. Tube 11 has a significantly larger internal diameter than does tube 12. The relative sizes of tubes 11 and 12 may correspond, for example, to the size of the minimum distance between the recesses between the corrugations of a prior art collapse-resistant tube and the depth of the corrugations respectively. The structure of FIG. 1 has been found to resist collapse to a level greater than that of commercially available crenellated, collapse-resistant tubes. Specifically, during testing, prior art collapse-resistant tubes exhibited kinks under pressures from which tubes of the type shown in FIG. 1 completely recovered.

Figure 2:
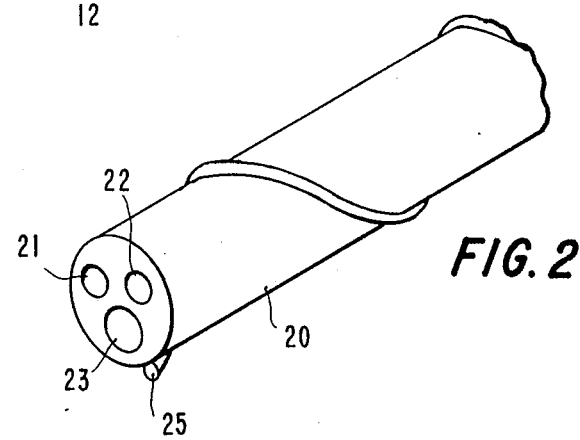

Importantly, inner tube 13 of the catheter of FIG. 1 has a smooth surface. Thus, collapse-resistant catheters as shown in FIG. 1 can be made in a multilumen form as shown in FIG. 2. Specifically, FIG. 2 shows a catheter having a tube 20 of a multilumen configuration including lumens 21, 22, and 23. Such lumens can be used in traditional fashion to provide access for optical fibers, guide wires, etc. But the catheter also includes spiral tube 25 which provides a collapse-resistant function as does tube 12 of FIG. 1.

Spiral tube 12 or 25 provides for an additional function as well. It permits the introduction of an additional fluid if a fixture for accessing the tube is attached.

Figure 3:
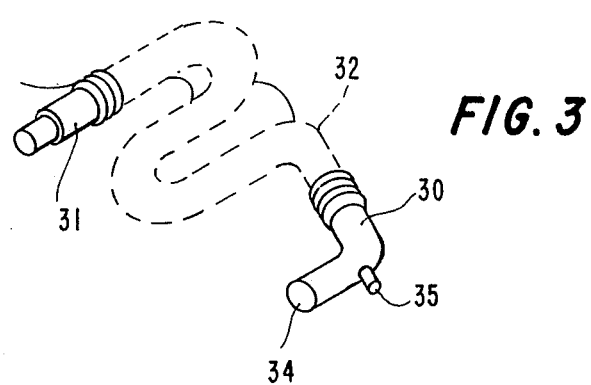
FIG. 3 is a schematic representation of a prior art collapse-resistant tube for air delivery.

For relatively large diameter air delivery collapse-resistant tubing, conventional fixtures can be used at either end of the tube. FIG. 3 shows conventional fittings 30 and 31 for the proximal and distal ends respectively of a prior art corrugated air delivery tube 32. The fixtures shown provide for the input of air at input port 34 and for insertion of an additional tube at input port 35. A fitting of the type identified at 30 in FIG. 3 is adapted so that input port 35 would communicate with spiral tube 12 of FIG. 1. The fitting is adapted to access multilumen catheters with the structure of FIG. 2 in a manner similar to fixtures for accessing presently available multilumen catheters.

Collapse-resistant tubing employing spiral external tubes can be made of a size to permit insertion into the human body. Specifically the center tube single or multilumen can be made with a diameter of 0.125 inch with the spiral tube being one-eighth that diameter or 0.009 inch. It is contemplated that the spiral would be tightly wound about the center tube for applications where insertion into the body is necessary. But the ideal slope for the spiral is expected to be different for different applications.

Figure 4:
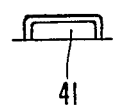
FIGS. 4, 5, and 6 are cross sections of spiral shaped second tubes for providing collapse-resistance.
Figure 5:
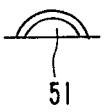
Figure 6:
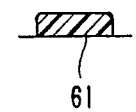

The invention has been described in terms of a spiral tube shown as having a circular cross section. It is to be understood that the spiral tube may have an oval, rectangular, semicircular, etc. shape and may be solid for applications where the spiral tube is not required for delivery of fluids. FIGS. 4, 5 and 6 show spiral tubes 41, 51, and 61 of rectangular, oval, and rectangular-solid configurations respectively.

Spiral tubes are fabricated at the same time a center tube is extruded by a coextrusion procedure employing a second extrusion die which travels in a circular path about the main extrusion die which configures the center tube. The second extrusion die is mounted on the face of a plate which is driven externally conveniently by a perimeter gear arrangement. The plate is adapted to receive the main die along a center aperture and to rotate the second die along an orbital path to coextrude the spiral tube along the wall of the center tube. The angular velocity of the second (planetary) die and the rate of extrusion of the center tube determines the slope of the spiral.

Figure 7:
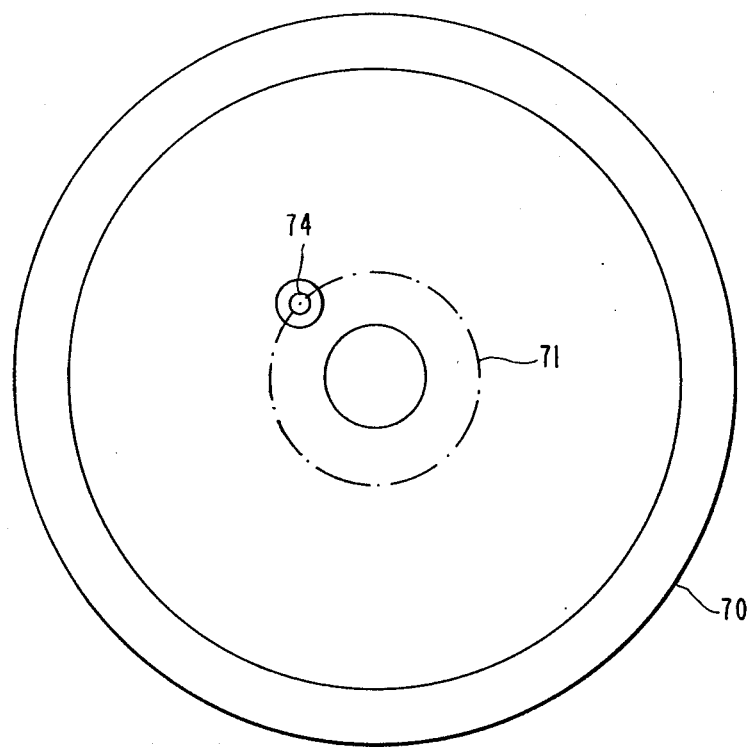
FIGS. 7 and 8 are end and cross section views of portions of extrusion apparatus for making spiral-shaped, collapse-resistant catheters.

FIG. 7 shows a circular plate 70 adapted to receive a first extrusion die 72 along its center axis and to receive a planetary (second) die 73 in an orbital position. Rotation of the plate as extrudate is metered into a center tube along an orthogonal path aligned with the axis of the plate results in the delivery of extrudate to a die which follows a spiral path with respect to the advancing center tube. The extrudate is delivered to the rotating plate into a circular channel located at the position of imaginary circle 71 in the underside of plate 70 as viewed in FIG. 7. An extrusion input port (not shown)

moves extrudate in conventional fashion to the circular channel to provide a continuous stream of extrudate to the channel as the plate (70) rotates.

The second die 73 is secured to plate 70 at aperture 74. Aperture 74 has an internal thread and communicates with the circular channel. The second die is secured to plate 70 at aperture 74 and thus is adapted to communicate with the circular channel.

The second die includes a center channel and pin arrangement adapted to configure the extrudate into the spiral tube in conventional fashion.

Figure 8:
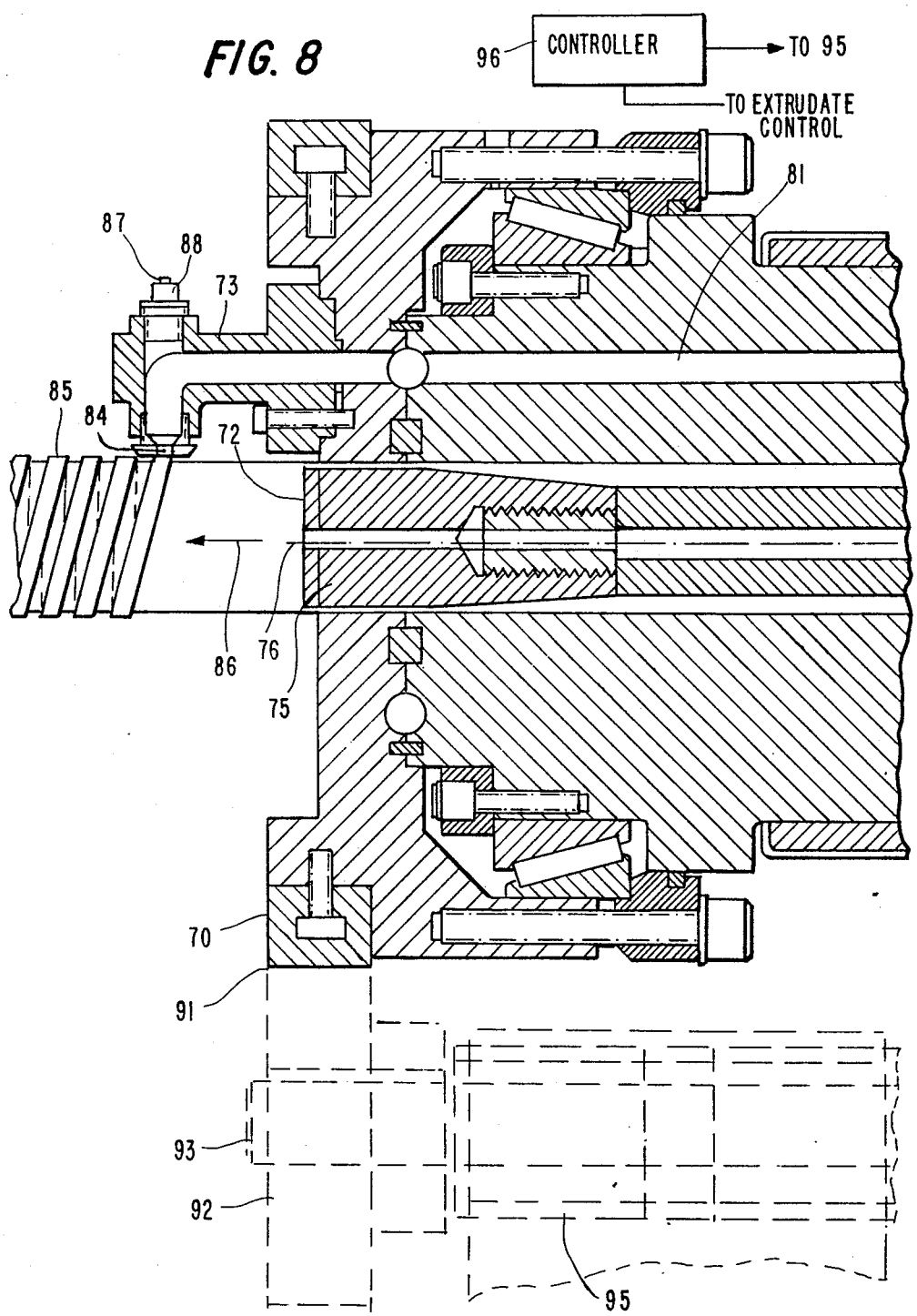

FIG. 8 shows plate 70 as well as the main and second dies in cross section. Plate 70 is shown positioned vertically with the main die, designated 75, aligned horizontally along the center axis 76 of the plate as viewed in FIG. 8. The planetary or second die 73 has a t-shaped geometry the base of which is secured at 74 so that extrudate in a supply channel 81 is fed through die 73 regardless of the position of die 73 with respect to the cirdular channel at circle 71 of FIG. 7. The extrudate exits die 73 at an exit port 84 and forms spiral 85 as the, now formed, center tube moves to the left as indicate by arrow 86 in FIG. 8.

Die 73 includes a pin-receiving port 87 adapted to receive a pin 88. With pin 87 in place, the spiral 85 is formed as a tube in conventional fashion. In the absence of pin 87, spiral 85 is formed as a solid. The shape of the spiral is controlled by the shape of the exit port 84 of die 73. The slope of the spiral is determined by the rate at which the center tube is advanced along axis 76 to the left as indicated by arrow 86.

The periphery of plate 70 includes a gear arrangement indicated at 91. The gear arrangement mates with gear 92 which is mounted on shaft 93. Shaft 93 is driven by motor 95. Controller 96 is adapted to coordinate the rotation of plate 70, the extrudate delivery and the rotation of die 73.

It is to be understood that different materials can be utilized to form the different tubes and lumens herein. Thus, the center tube, or a single lumen therein, may be made of an abrasion-resistant material and the second tube or other lumen may be made of biocompatible material.

What is claimed is:

1. A collapse-resistant catheter comprising a central tube, said tube having a second tube integral with its exterior surface, said second tube having a hollow spiral geometry of a configuration open at both ends and providing a collapse-resistant function by its geometry alone, said central and said second tube being coextruded.

2. A catheter in accordance with claim 1 wherein said central and second tubes have a ratio of diameters of about eight to one.

3. A catheter in accordance with claim 1 wherein said central tube includes a plurality of lumens.

4. A catheter in accordance with claim 2 wherein said central tube has a diameter of 0.125 inch and said spiral tube has a diameter of 0.008 inch.

5. A catheter in accordance with claim 1 wherein said second tube is hollow and has a circular shape.

6. A catheter in accordance with claim 1 wherein said second tube is hollow and has a semicircular shape.

* * * * *